(12) United States Patent
Röchling et al.

(10) Patent No.: US 6,602,823 B1
(45) Date of Patent: Aug. 5, 2003

(54) AGROCHEMICAL FORMULATIONS

(75) Inventors: Andreas Röchling, Langenfeld (DE); Anne Suty-Heinze, Langenfeld (DE); Karl Reizlein, Köln (DE); Udo Reckmann, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/857,784

(22) PCT Filed: Dec. 6, 1999

(86) PCT No.: PCT/EP99/09528

§ 371 (c)(1),
(2), (4) Date: Jun. 8, 2001

(87) PCT Pub. No.: WO00/35278

PCT Pub. Date: Jun. 22, 2000

(30) Foreign Application Priority Data

Dec. 16, 1998 (DE) ......................... 198 57 963

(51) Int. Cl.[7] .......................... A01N 3/02; A01N 43/54; A01N 43/647; A01N 43/72; A01N 43/653
(52) U.S. Cl. ................... 504/116.1; 504/136; 504/139; 504/223; 504/272; 504/273
(58) Field of Search ................... 514/229.2; 504/116.1, 504/136, 139, 223, 272, 273

(56) References Cited

U.S. PATENT DOCUMENTS 5,705,476 A * 1/1998 Hoffarth ..................... 510/535

FOREIGN PATENT DOCUMENTS

| CA | 2099631 | | 1/1994 |
| EP | 0 355 759 | | 2/1990 |
| EP | 0 681 865 | | 11/1995 |
| GB | 2269102 | * | 2/1994 |
| WO | 97/04653 | | 2/1997 |
| WO | 98/35553 | | 8/1998 |

* cited by examiner

Primary Examiner—Alton Pryor
(74) Attorney, Agent, or Firm—Richard E. L. Henderson; Joseph C. Gil; John E. Mrozinski, Jr.

(57) ABSTRACT

Agrochemical formulations comprising
  a) at least one agrochemically active compound,
  b) 2-ethyl-hexanol alkoxylate of the formula

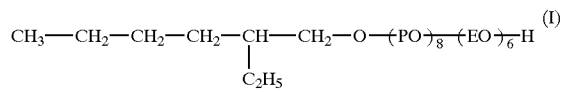

in which
P represents

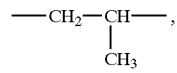

E represents $-CH_2-CH_2-$ and
the numbers 8 and 6 are average values and
  c) optionally additives,
a process for preparing these formulations and their use for applying the active compounds they comprise are described.

24 Claims, No Drawings

AGROCHEMICAL FORMULATIONS

This application is a 371 of PCT/EP99/09528 filed Dec. 6, 1999.

FIELD OF THE INVENTION

The present invention relates to novel agrochemical formulations based on certain 2-ethyl-hexanol alkoxylates, to a process for preparing these formulations and to their use for applying the agrochemically active compounds they comprise.

BACKGROUND OF THE INVENTION

Numerous formulations of crop treatment agents comprising the fatty alcohol ethoxylates as wetting agents and/or penetrants have already been disclosed (cf. EP-A 0 579 052). The activity of these preparations is good. However, they have the disadvantage that in some cases a lot of foam is formed on stirring with water.

Furthermore, formulations of agrochemicals comprising fatty alcohol propoxylates as formulation auxiliaries have already been described (cf. U.S. Pat. No. 3,673,087). However, the properties of these preparations are likewise not always satisfactory, since propoxylates having a relatively long alkyl moiety are sparingly soluble in water and thus have a tendency to form deposits.

Moreover, it is known that mixtures of fatty alcohol ethoxylates and propoxylates and their copolymers can be employed as low-foam wetting agents for formulating active compounds in crop protection (cf. EP-A 0 681 865). However, in practice, the properties of such preparations are in some instances unsatisfactory.

SUMMARY OF THE INVENTION

Agrochemical formulation comprise an agrochemically active compound, a 2-ethyl-hexanol alkoxylate of the formula

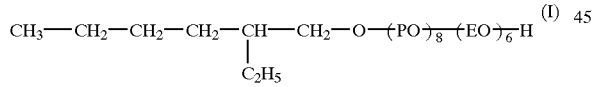

wherein P represents —CH$_2$—CH(CH$_3$), E represent —CH$_2$—CH$_2$—, and the numbers 8 and 6 are average values, and optionally additives.

DETAILED DESCRIPTION

This invention, accordingly, provides novel agrochemical formulations comprising a) at least one agrochemically active compound,
b) 2-ethyl-hexanol alkoxylate of the formula

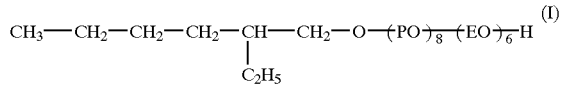

in which

P represents

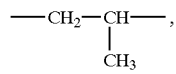

E represents —CH$_2$—CH$_2$— and
the numbers 8 and 6 are average values and
c) optionally additives.

Furthermnore, it has been found that the agrochemical formnulations according to the invention can be prepared by mixing at least one agrochemically active compound
with 2-ethyl-hexanol alkoxylate of the formula (I) and
optionally with additives.

Finally, it has been found that the agrochemical formulations according to the invention are highly suitable for applying the active compounds they comprise to plants and/or their habitat.

It is extremely surprising that the formulations according to the invention are, with respect to their properties, considerably superior to the prior-art preparations of the most similar composition. Besides, based on the teaching of EP-A 0 681 865, it was to be assumed that a mixture of different alkoxylates is required so that the resulting compositions meet all the requirements of practice. However, contrary to expectations, this is not the case. Specifically the presence of 2-ethyl-hexanol alkoxylate of the formula (I) is sufficient to generate formulations having the desired property profile.

The formulations according to the invention have a number of advantages. Thus, on mixing the formulations according to the invention with water, only very little foam is formed. Furthermore, the formulations have a favourable effect on the biological activity of the active components they comprise. Moreover, it is advantageous that sparingly water-soluble active compounds in the formulations according to the invention show a reduced tendency to crystallize on dilution with water.

The formulations according to the invention comprise one or more agrochemically active compounds. Here, agrochemically active compounds are to be understood as meaning all substances which are customary for the treatment of plants. Fungicides, bactericides, insecticides, acaricides, nematicides, herbicides, plant growth regulators, plant nutrients and repellents may be mentioned as being preferred.

Examples of fungicides which may be mentioned are:

2-aminobutane; 2-anilino-4-methyl-6-cyclopropyl-pyrimidine; 2',6'-dibromo-2-methyl-4'-trifluoromethoxy-4'-trifluoromethyl-1,3-thizole-5-carboxanilide; 2,6-dichloro-N-(4-trifluoromethylbenzyl)-benzamide; (E)-2-methoximino-N-methyl-2-(2-phenoxyphenyl) acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino [alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), quinoxyfen, tebuconazole, tecloftalam, tecnazene, tetraconazole, thiabendazole, thicyofen, thiophanate-methyl, thiram, toiclophos-methyl, tolylfluanid, triadimefon, triadimenol, triazoxide, trichlamide, tricyclazole, tridemorph, triflumizole, triforine, triticonazole, validamycin A, vinclozolin, zineb, ziram, 8-tert-butyl-2-(N-ethyl-N-n-propyl-amino)-methyl-1,4-dioxa-spiro-[4,5]decane, N-(R)-[1-(4-chlorophenyl)-ethyl]-2,2-dichloro-1-ethyl-3t-methyl-1r-cyclopropanecarboxamide (diastereomer mixture or individual isomers), 1-methylethyl [2-methyl-1-[[[1-(4-methylphenyl)-ethyl]-amino]-carbonyl]-propyl]-carbamate, N-(2,3-dichloro-4-hydroxy)-1-methyl-cyclohexyl-1-carboxanilide, 2-[2-(1-chloro-cyclopropyl)-3-(2-chlorophenyl)-2-hydroxypropyl]-2,4-dihydro-[1,2,4]-triazole-3-thione, 1-(3,5-dimethyl-isoxazole-4-sulphonyl)-2-chloro-6,6-difluoro-[1,3]-dioxolo-[4,5-f]-benzimidazole and (5,6-dihydro-1,4,2-dioxazin-3-yl)-{2-[[6-(2-chloro-phenoxy)-5-fluoro-4-pyrimidinyl]-oxy]phenyl}-methanone-O-methyloxime.

Examples of Bactericides Which may be Mentioned are:
bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Examples of Insecticides, Acaricides and Nematicides Which may be Mentioned are:
abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chloroethoxyfos, chlorofenvinphos, chlorofluazuron, chloromephos, N-[(6-chloro-3-pyridinyl)-methyl]-N'-cyano-N-methyl-ethanimidamide, chloropyrifos, chloropyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, ometboate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, transfluthrin, triarathen, triazophos, triazuron, trichlorfon, triflumuron, trimethacarb, vamidothion, XMC, xylylcarb, zetamethrin.

Examples of herbicides which may be mentioned are: anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuiron, cinosulfuron, metsulfuron-methyl, nicosulfuron, primisulfuron, pyrazosulfuron-ethyl, thifensulfuron-methyl, triasulfuron and tri-benuron-methyl; thiolcarbamates such as, for example, butylates, cycloates, diallates, EPTC, esprocarb, molinates, prosulfocarb, thiobencarb and triallates; triazines such as, for example, atrazine, cyanazine, simazine, simetryne, terbutryne and terbutylazine; triazinones such as, for example, hexazinone, metamitron and metribuzin; others such as, for example, aminotriazole, 4-amino-N-(1,1-dimethylethyl)-4,5-dihydro-3-(1-methylethyl)-5-oxo-1H-1,2,4-triazole-1-carboxamide, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Plant growth regulators which may be mentioned are chlorocholine chloride and ethephon.

Examples of plant nutrients which may be mentioned are customary inorganic or organic fertilizers for providing plants with macro- and/or micronutrients.

Examples of repellents which may be mentioned are diethyltolylamide, ethylhexanediol and butopyronoxyl.

Particularly preferred examples of fuingicides which may be mentioned are the active compounds of the formulae

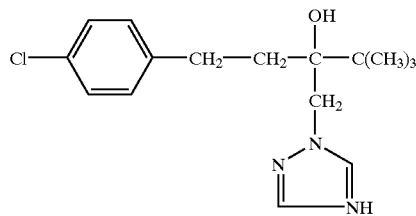

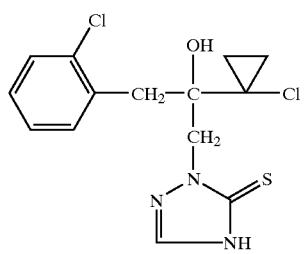

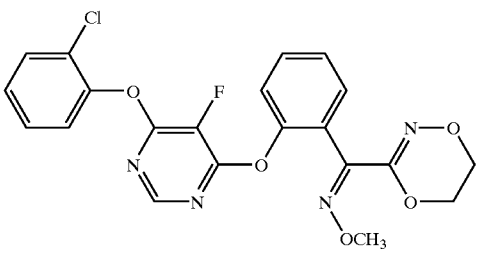

The formulations according to the invention furthermore comprise 2-ethyl-hexanol alkoxylate of the formula (I). In this formula, the numbers 8 and 6 are average values. Thus, the 2-ethyl-hexanol alkoxylate of the formula (I) is a substance mixture having preferably 8 propylene oxide and 6 ethylene oxide units.

The 2-ethyl-hexanol alkoxylate of the formula (I) is already known (cf. EP-A 0 681 865).

Suitable additives which may be present in the formulations according to the invention are all customary formulation auxiliaries such as, for example, organic solvents, emulsifiers, dispersants, preservatives, colourants, fillers and also water.

Suitable organic solvents are all customary organic solvents which dissolve the agrochemically active compounds used well. These are preferably aliphatic and aromatic, optionally halogenated hydrocarbons, such as toluene, xylene, Solvesso®, mineral oils, such as white spirit, petroleum, alkylbenzenes and spindle oil, furthermore carbon tetrachloride, chloroform, methylene chloride and dichloromethane, moreover esters, such as ethyl acetate, furthermore lactones, such as butyrolactone, moreover lactams, such as N-methylpyrrolidone, N-octylpyrrolidone and N-methylcaprolactam, and also alkanecarboxamides, such as N,N-dimethyl-decanecarboxamide and N,N-dimethyl-octanecarboxamide, and also dimethylformamide.

Suitable emulsifiers are customary surfactants which are present in formulations of agrochemically active compounds. Examples which may be mentioned are ethoxylated nonylphenols, polyethylene glycol ethers of linear alcohols, reaction products of alkylphenols with ethylene oxide and/or propylene oxide, furthermore fatty esters, alkylsulfonates, alkyl sulfates, aryl sulfates, ethoxylated arylalkylphenols, such as, for example, tristyryl-phenol ethoxylate having on average 16 ethylene oxide units per molecule, furthermore ethoxylated and propoxylated arylalkylphenols and sulfated or phosphated arylalkylphenol ethoxylates or ethoxy- and propoxylates.

Suitable dispersants are all substances which are customarily used for this purpose in crop protection compositions. These are preferably natural and synthetic water-soluble polymers, such as gelatin, starch and cellulose derivatives, in particular cellulose esters and cellulose ethers, further polyvinyl alcohol, polyvinylpyrrolidone, polyacrylic acid, polymethacrylic acid and copolymers of (meth)acrylic acid and (meth)acrylic esters, and furthermore also copolymers of methacrylic acid and methacrylic ester which are neutralized with alkali metal hydroxide.

Suitable preservatives are all substances which are customarily present for this purpose in crop treatment compositions. Examples which may be mentioned are Preventol® and Proxel®.

Suitable colourants are all inorganic or organic colourants which are customarily used for preparing crop protection compositions. Examples which may be mentioned are titanium dioxide, colour black, zinc oxide and blue pigments.

Suitable fillers are all substances which are customarily used for this purpose in crop protection compositions. These are preferably inorganic particles, such as carbonates, silicates and oxides having an average particle size of from 0.005 to 5 µm, particularly preferably from 0.02 to 2 µm. Examples which may be mentioned are silicon dioxide, so-called finely divided silicic acid, silica gels, and natural and synthetic silicates and alumosilicates.

The content of the individual components in the formulations according to the invention can be varied within a relatively wide range. Thus, the concentrations

- of agrochemically active compounds are generally between 1 and 90% by weight, preferably between 5 and 30% by weight
- of 2-ethyl-hexanol alkoxylate of the formula (I) are generally between 1 and 90% by weight, preferably between 10 and 50% by weight and
- of additives are generally between 0 and 98% by weight, preferably between 20 and 85% by weight.

The agrochemical formulations according to the invention are prepared by mixing the components in the particular ratios desired. If the agrochemically active compound is a solid, it is generally employed in finely ground form or in the form of a solution or suspension in an organic solvent. If the agrochemically active compound is liquid, it is frequently not necessary to use an organic solvent. It is furthermore possible to employ a solid agrochemically active compound in the form of a melt.

When carrying out the process according to the invention, the temperatures can be varied within a certain range. In general, the process is carried out at temperatures between 0° C. and 80° C., preferably between 10° C. and 60° C.

The process according to the invention is generally carried out by mixing 2-ethylhexanol alkoxyate of the formula (I) with one or more agrochemically active compounds and, if appropriate, with additives, by stirring intensively. The components can be mixed with one another in any order. In a preferred variant of the process according to the invention, however, 2-ethyl-hexanol alkoxylate of the formula (I) is mixed with one or more agrochemically active compounds and with other additives, and the resulting premix is dispersed in water, giving emulsions, suspensions or solutions.

Suitable for carrying out the process according to the invention is customary apparatus which are employed for preparing agrochemical formulations.

The agrochemical formulations according to the invention can be applied in the forms of preparation which are customary for liquid preparations, either as such or after prior dilution with water, i.e., for example, as emulsions, suspensions or solutions. The application is carried out by customary methods, i.e., for example, by spraying, watering or injecting.

The application rate of the agrochemical formulations according to the invention can be varied within a relatively wide range. It depends on the respective agrochemically active compounds and their content in the formulations.

Using the formulations according to the invention, it is possible to apply agrochemically active compounds in a particularly advantageous manner to plants and/or their habitat. Undesired formation of foam both during dilution of the concentrates with water and during spraying is substantially avoided. Moreover, the tendency towards crystallization of solid active compounds is reduced and the biological activity of the active components is increased in comparison to customary formulations.

The invention is illustrated by the examples below.

PREPARATION EXAMPLES

Example 1

To prepare a formulation according to the invention, 10 g of active compound of the formula

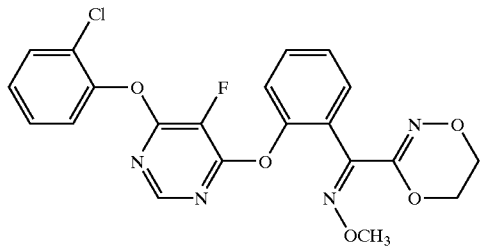

are initially mixed with 40 g of butyrolactone and then with 50 g of 2-ethyl-hexanol alkoxylate of the formula (I)

with stirring at room temperature. After the addition has ended, the mixture is stirred at room temperature for another 30 minutes. This gives a homogeneous solution.

Example 2

To prepare a formulation according to the invention, 10 g of active compound of the formula

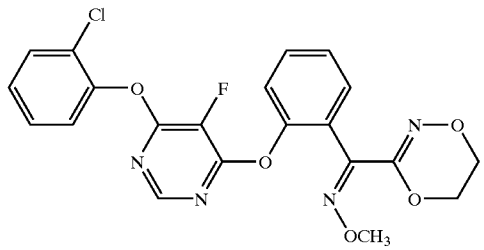

are initially mixed with 35 g of butyrolactone and then with 35 g of 2-ethyl-hexanol alkoxylate of the formula (I) and 20 g of tristyryl-phenol ethoxylate having an average of 16 ethylene oxide units per molecule with stirring at room temperature. After the addition has ended, the mixture is stirred at room temperature for another 30 minutes. This gives a homogeneous solution.

Comparative Example I

To prepare a conventional formulation, 10 g of active compound of the formula

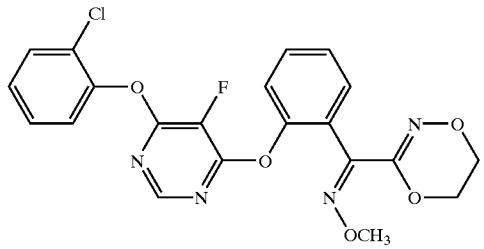

are initially mixed with 70 g of butyrolactone and then with 20 g of tristyryl-phenol ethoxylate having an average of 16 ethylene oxide units per molecule with stirring at room temperature. After the addition has ended, the mixture is stirred at room temperature for another 30 minutes. This gives a homogeneous solution.

USE EXAMPLES

Example A

Erysiphe Test (Barley)/protective

To prepare a ready-to-use preparation of active compound, the concentrate is in each case diluted with water to the desired concentration.

To test for protective activity, young plants are sprayed with the preparation of active compound at the stated application rate.

1 day after spraying, the plants are dusted with spores of *Erysiphe graminis* f.sp. *hordei*.

The plants are placed in a greenhouse at a temperature of approximately 18° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Formulations, active compound application rates and test results are shown in the tables below.

TABLE A-1

Erysiphe test (barley)/protective

| Formulation according to Example | Active compound application rate in g/ha | Efficacy in % |
| --- | --- | --- |
| Known: | | |
| (I) | 62.5 | 76 |
| According to the invention: | | |
| (1) | 62.5 | 90 |

TABLE A-2

Erysiphe test (barley)/protective

| Formulation according to Example | Active compound application rate in g/ha | Efficacy in % |
| --- | --- | --- |
| Known: | | |
| (I) | 62.5 | 72 |
| According to the invention: | | |
| (2) | 62.5 | 89 |

Example B

Erysiphe Test (Wheat)/curative

To prepare a ready-to-use preparation of active compound, the concentrate is in each case diluted with water to the desired concentration.

To test for curative activity, young plants are dusted with spores of *Erysiphe graminis* f.sp. *tritici*. 48 hours after the inoculation, the plants are sprayed with the preparation of active compound at the stated application rate.

The plants are placed in a greenhouse at a temperature of approximately 18° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

Formulations, active compound application rates and test results are shown in the tables below.

TABLE B-1

Erysiphe test (wheat)/curative

| Formulation according to Example | Active compound application rate in g/ha | Efficacy in % |
| --- | --- | --- |
| Known: | | |
| (I) | 62.5 | 38 |
| According to the invention: | | |
| (1) | 62.5 | 86 |

TABLE B-2

Erysiphe test (wheat)/curative

| Formulation according to Example | Active compound application rate in g/ha | Efficacy in % |
| --- | --- | --- |
| Known: | | |
| (I) | 62.5 | 60 |
| According to the invention: | | |
| (2) | 62.5 250 ppm | 77 |

Example C

*Leptosphaeria nodorum* Test (Wheat)/curative

To prepare a ready-to-use preparation of active compound, the concentrate is in each case diluted with water to the desired concentration.

To test for curative activity, young plants are sprayed with a conidia suspension of *Leptosphaeria nodorum*. The plants remain in an incubation cabin at 20° C. and 100% relative atmospheric humidity for 48 hours and are then sprayed with the preparation of active compound at the stated application rate.

The plants are placed in a greenhouse at a temeprature of approximately 22° C. and a relative atmospheric humidity of approximately 80%.

Evaluation is carried out 10 days after the inoculation. 0% means an efficacy which corresponds to that of the control, whereas an efficacy of 100% means that no infection is observed.

Formulations, active compound application rates and test results are shown in the table below.

TABLE C

*Leptosphaeria nodorum* test (wheat)/curative

| Formulation according to Example | Active compound application rate in g/ha | Efficacy in % |
| --- | --- | --- |
| Known: | | |
| (I) | 62.5 | 87 |

TABLE C-continued

Leptosphaeria nodorum test (wheat)/curative

| Formulation according to Example | Active compound application rate in g/ha | Efficacy in % |
|---|---|---|
| According to the invention: | | |
| (1) | 62.5 | 100 |

Example D
*Pyrenophora teres* Test (Barley)/curative

To prepare a ready-to-use preparation of active compound, the concentrate is in each case diluted with water to the desired concentration.

To test for curative activity, young plants are sprayed with a conidia suspension of *Pyrenophora teres*. The plants remain in an incubation cabin at 20° C. and 100% relative atmospheric humidity for 48 hours. The plants are then sprayed with the preparation of active compound at the stated application rate.

The plants are placed in a greenhouse at a temperature of approximately 20° C. and a relative atmospheric humidity of approximately 80%.

Evaluation is carried out 7 days after the inoculation. 0% means an efficacy which corresponds to that of the control, whereas an efficacy of 100% means that no infection is observed.

Formulations, active compound application rates and test results are shown in the table below.

TABLE D

*Pyrenophora teres* test (barley)/curative

| Formulation according to Example | Active compound application rate in g/ha | Efficacy in % |
|---|---|---|
| Known: | | |
| (I) | 62.5 | 54 |
| According to the invention: | | |
| (1) | 62.5 | 73 |

What is claimed is:

1. An agrochemical formulation consisting essentially of
(a) an agrochemically active compound,
(b) 2-ethyl-hexanol alkoxylate of the formula (I)

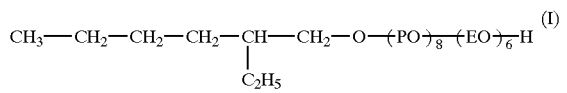

wherein
P represents

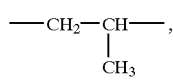

E represents —CH$_2$—CH$_2$—, and
the numbers 8 and 6 represent that the 2-ethyl-hexanol alkoxylate has on average 8 PO units and on average 6 EO units, and (c) optionally additives.

2. An agrochemical formulation consisting essentially of
(a) an agrochemically active compound of the formula

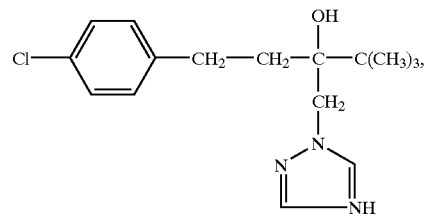

(b) 2-ethyl-hexanol alkoxylate of the formula (I)

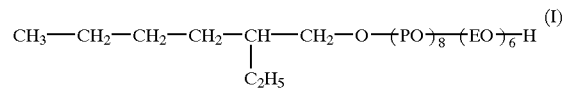

wherein
P represents

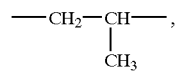

E represents —CH$_2$—CH$_2$—, and
the numbers 8 and 6 represent that the 2-ethyl-hexanol alkoxylate has on average 8 PO units and on average 6 EO units, and (c) optionally additives.

3. A process for preparing the agrochemical formulation of claim 2 comprising mixing the agrochemically active compound with a 2-ethyl-hexanol alkoxylate of the formula (I).

4. A method comprising applying the agrochemical formulation of claim 2 to a plant and/or its habitat.

5. An agrochemical formulation of claim 2 consisting essentially of between 5 and 30% by weight of the agrochemically active compound, 10 and 50% by weight of the 2-ethyl-hexanol alkoxylate of the formula (I), and between 20 and 85% by weight of the additive.

6. An agrochemical formulation of claim 2 wherein the additive is selected from the group consisting of organic solvents, emulsifiers, dispersants, preservatives, colorants, fillers, water, and combinations thereof.

7. An agrochemical formulation consisting essentially of
(a) an agrochemically active compound of the formula,

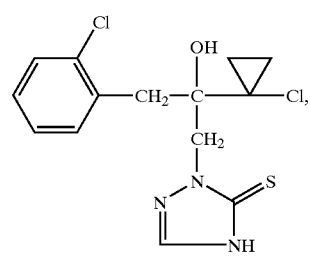

(b) 2-ethyl-hexanol alkoxylate of the formula (I)

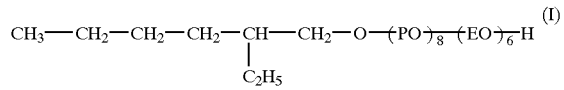

wherein
P represents

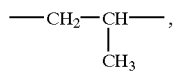

E represents —CH$_2$—CH$_2$—, and
the numbers 8 and 6 represent that the 2-ethyl-hexanol alkoxylate has on average 8 PO units and on average 6 EO units, and
(c) optionally additives.

8. A process for preparing the agrochemical formulation of claim 7 comprising mixing the agrochemically active compound with a 2-ethyl-hexanol alkoxylate of the formula (I).

9. A method comprising applying the agrochemical formulation of claim 7 to a plant and/or its habitat.

10. An agrochemical formulation of claim 7 consisting essentially of between 5 and 30% by weight of the agrochemically active compound, 10 and 50% by weight of the 2-ethyl-hexanol alkoxylate of the formula (I), and between 20 and 85% by weight of the additive.

11. An agrochemical formulation of claim 7 wherein the additive is selected from the group consisting of organic solvents, emulsifiers, dispersants, preservatives, colorants, fillers, water, and combinations thereof.

12. An agrochemical formulation consisting essentially of
(a) an agrochemically active compound of the formula

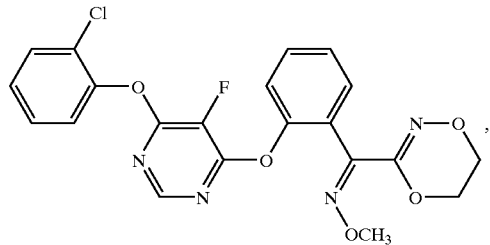

(b) 2-ethyl-hexanol alkoxylate of the formula (I)

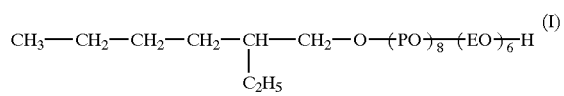

wherein
P represents

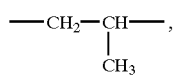

E represents —CH$_2$—CH$_2$—, and
the numbers 8 and 6 represent that the 2-ethyl-hexanol alkoxylate has on average 8 PO units and on average 6 EO units, and
(c) optionally additives.

13. A process for preparing the agrochemical formulation of claim 12 comprising mixing the agrochemically active compound with a 2-ethyl-hexanol alkoxylate of the formula (I).

14. A method comprising applying the agrochemical formulation of claim 12 to a plant and/or its habitat.

15. An agrochemical formulation of claim 12 consisting essentially of between 5 and 30% by weight of the agrochemically active compound, 10 and 50% by weight of the 2-ethyl-hexanol alkoxylate of the formula (I), and between 20 and 85% by weight of the additive.

16. An agrochemical formulation of claim 12 wherein the additive is selected from the group consisting of organic solvents, emulsifiers, dispersants, preservatives, colorants, fillers, water, and combinations thereof.

17. An agrochemical formulation consisting essentially of
(a) between 1 and 90% by weight of an agrochemically active compound,
(b) 1 and 90% by weight of a 2ethyl-hexanol alkoxylate of the formula (I)

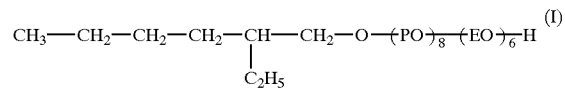

wherein
P represents

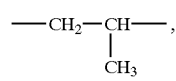

E represents —CH$_2$—CH$_2$—, and
the numbers 8 and 6 represent that the 2-ethyl-hexanol alkoxylate has on average 8 PO units and on average 6 EO units
(c) between 0 and 98% by weight of an additive.

18. An agrochemical formulation of claim 17 wherein the agrochemically active compound is selected from the group consisting of a fungicide, a bactericide, an insecticide, an acaricide, a nematicide, an herbicide, a plant growth regulator, a plant nutrient, and a repellent.

19. An agrochemical formulation according to claim 17 wherein the agrochemically active compound is selected from the group consisting of an insecticide, an acaricide, and a nematicide.

20. An agrochemical formulation of claim 17 wherein the agrochemically active compound is a fungicide.

21. An agrochemical formulation of claim 20 wherein the fungicide is selected from the group consisting of

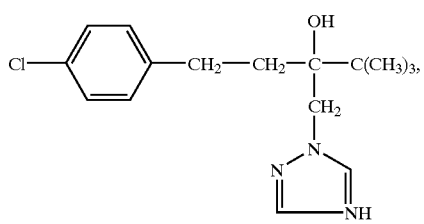

-continued

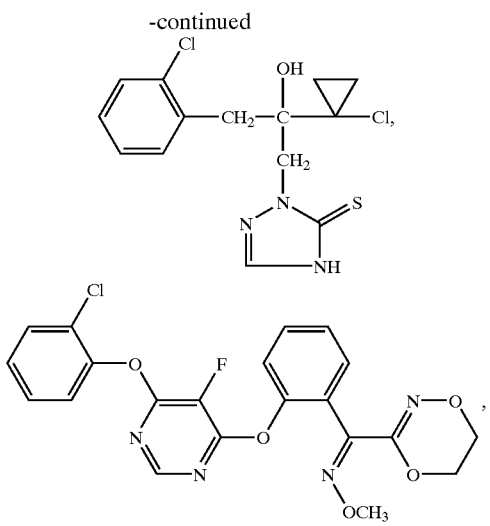

and combinations thereof.

22. An agrochemical formulation consisting essentially of
(a) between 1 and 90% by weight of an agrochemically active compound selected from the group consisting of an anilide, an aryloxyalkanoic acid, an aryloxy-phenoxy-alkanoic ester, an azinone, a chloroacetanilide, a dinitroaniline, a diphenyl ether, a urea, a hydroxylamine, an imidazolinone, a nitrile, an oxyacetamide, a sulphonylurea, a throlcarbamate, a triazine, a triazinone, aminotriazole, 4-amino-N-(1,1-dimethylethyl)-4,5-dihydro-3-(1-methylethyl)-5-oxo-1H-1,2,4-triazole-1-carboxamide, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate, and tridiphane,
(b) 1 and 90% by weight of a 2-ethyl-hexanol alkoxylate of the formula (I)

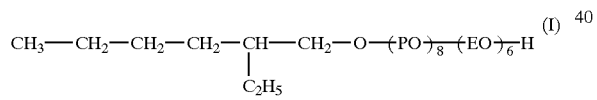

wherein
P represents

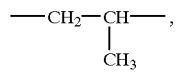

E represents —CH$_2$—CH$_2$—, and
the numbers 8 and 6 represent that the 2-ethyl-hexanol alkoxylate has on average 8 PO units and on average 6 EO units, and (c) between 0 and 98% by weight of an additive.

23. An agrochemical formulation consisting essentially of
(a) a plant growth regulator selected from the group consisting of chlorocholine chloride, ethephon, and mixtures thereof,
(b) 1 and 90% by weight of a 2-ethyl-hexanol alkoxylate of the formula (I)

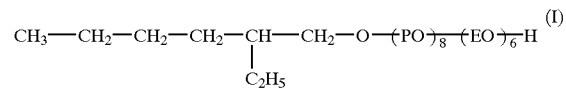

wherein
P represents

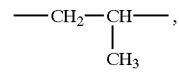

E represents —CH$_2$—CH$_2$—, and
the numbers 8 and 6 represent that the 2-ethyl-hexanol alkoxylate has on average 8 PO units and on average 6 EO units, and (c) between 0 and 98% by weight of an additive.

24. An agrochemical formulation consisting essentially of
(a) a repellant selected from the group consisting of diethyltolylamide, ethylhexanedial, butopyronoxyl, and mixtures thereof,
(b) 1 and 90% by weight of a 2-ethyl-hexanol alkoxylate of the formula (I)

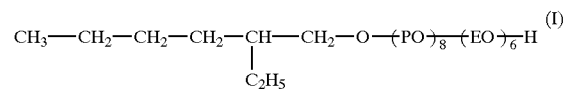

wherein
P represents

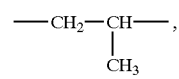

E represents —CH$_2$—CH$_2$—, and
the numbers 8 and 6 represent that the 2-ethyl-hexanol alkoxylate has on average 8 PO units and on average 6 EO units, and (c) between 0 and 98% by weight of an additive.

* * * * *